(12) United States Patent
Hofmann et al.

(10) Patent No.: US 7,175,872 B2
(45) Date of Patent: Feb. 13, 2007

(54) PYRIDINIUM-BETAIN COMPOUNDS FOR USE AS TASTE MODULATORS

(75) Inventors: Thomas Hofmann, Münster-Roxel (DE); Harald Ottinger, Freiburg (DE); Oliver Frank, Münster (DE); Tomislav Soldo, Memmingen (DE); Imre Blank, Savigny (CH); Renaud Villard, Carrouge (CH); Fabien Robert, Divonne-les-Bains (FR)

(73) Assignee: Nestec S.A., Vevey (CH)

( * ) Notice: Subject to any disclaimer, the term of this patent is extended or adjusted under 35 U.S.C. 154(b) by 297 days.

(21) Appl. No.: 10/792,369

(22) Filed: Mar. 2, 2004

(65) Prior Publication Data

US 2004/0171648 A1    Sep. 2, 2004

Related U.S. Application Data

(63) Continuation of application No. PCT/EP02/10368, filed on Sep. 5, 2002.

(51) Int. Cl.
*A23L 1/22* (2006.01)
*A23L 1/226* (2006.01)
*C07D 405/00* (2006.01)
*C07D 211/72* (2006.01)

(52) U.S. Cl. ............ 426/535; 546/283.1; 546/300; 546/294; 426/536; 426/537

(58) Field of Classification Search ............ 546/283.1, 546/300, 294; 514/336; 426/535, 536, 537
See application file for complete search history.

*Primary Examiner*—Thomas McKenzie
*Assistant Examiner*—Binta Robinson
(74) *Attorney, Agent, or Firm*—Bell, Boyd & Lloyd LLC

(57) ABSTRACT

Pyridinium-Betain compounds of the general formula (A):

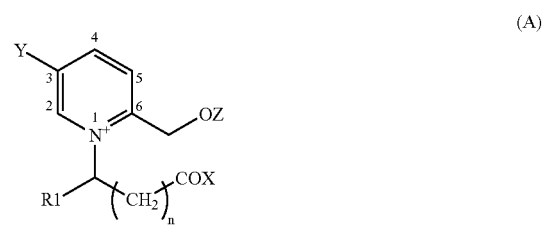

wherein R1 is H or a primary amino acids that is attached to the structure,
  X is OH or its ionized form O⁻,
  Y is OH, SH, or their ionized forms O⁻ and S⁻,
  Z is H, an alkyl group, or a glycosidic group, or a phosphate or ester derivative thereof, and
  n is an integer of 0 to 4 to represent the chain length of the compound.

A counter-ion is associated with these compounds and is preferably an ion of sodium, potassium, ammonium, calcium, magnesium, chloride, nitrate, carbonate, sulphate, phosphate, or the like. These compounds can be used as taste modifiers in various foodstuffs.

17 Claims, 5 Drawing Sheets

PYRIDINIUM-BETAIN COMPOUNDS FOR USE AS TASTE MODULATORS

CROSS-REFERENCE TO RELATED APPLICATIONS

This application is a continuation of International Application PCT/EP02/10368 filed Sep. 5, 2002, the content of which is expressly incorporated herein by reference thereto.

BACKGROUND

The present invention discloses new Pyridinium-Betain compounds and their use as taste modifying compounds or taste modulators.

The non-enzymatic reaction between reducing carbohydrates and amino acids, named as the Maillard reaction, is known to generate aroma, taste and browning compounds contributing to the sensory quality of thermally processed foods, such as processed meats, cereals, malt, coffee or cocoa. Compared to aroma-active volatiles such as these, however, the information available on culinary taste or taste modifying compounds generated during thermal food processing is as yet very fragmentary. The structures and sensory qualities of Maillard reaction products exhibiting bitter, salty, sweet or umami tastes, respectively, as well as components eliciting chemesthetic effects on the tongue such as, e.g., heating, cooling, astringency etc., have rarely been described.

Recently, a novel bioassay was developed, which is based on the determination of the taste threshold of reaction products in serial dilutions of HPLC fractions (Frank, O., Ottinger, H., Hofmann T. *J. Agric. Food Chem.* 2001, 49, 231–238; Ottinger, H., Bareth, A., Hofmann, T. *J. Agric. Food Chem.* 2001, 49, 1336–1344), to select the most intense taste compounds in a thermally treated solution of xylose and primary amino acids exhibiting intense bitter taste. By application of this so called Taste Dilution Analysis (TDA) as a screening procedure for the detection of as yet unknown taste-active compounds the previously unknown 3-(2-furyl)-8-[(2-furyl)methyl]-4-hydroxymethyl-1-oxo-1H,4H-quinolizinium-7-olate could be identified as the key taste-active compound (tastant) in the reaction mixture. This novel compound exhibits an intense bitter taste at a low detection threshold of 0.00025 mmol/kg water.

Despite this, however, there is very little information about compounds generated by Maillard reactions, even though these are tasteless but show taste-modifying properties. Thus, there is a need in the art for further compounds of these types so that the sensory quality of taste-active compounds can be enhanced or reduced as necessary.

SUMMARY OF THE INVENTION

The present invention relates to new Pyridinium-Betain compounds of the general formula (A):

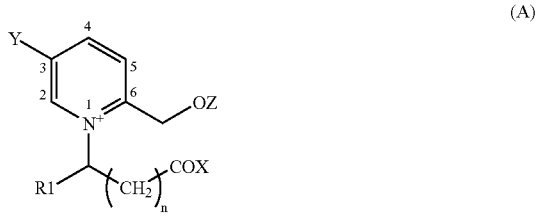

(A)

wherein R1 is H or a primary amino acids that is attached to the structure,

X is OH or its ionised form $O^-$,

Y is OH, SH, or their ionised forms $O^-$ and $S^-$,

Z is H, an alkyl group, or a glycosidic group, or a phosphate or ester derivative thereof, and n is an integer of 0 to 4 to represent the chain length of the compound.

A counter-ion is associated with these compounds and is preferably an ion of sodium, potassium, ammonium, calcium, magnesium, chloride, nitrate, carbonate, sulphate, phosphate, or the like.

The invention also relates to a food composition comprising a food and a Pyridinium-Betain compound according to the invention in a taste effective amount sufficient to enhance sweetness, saltiness or umami taste characteristics of the food or to reduce bitter taste characteristics of the food. Preferred foods for addition of this compound include chocolate, ice-cream, a beverage, a sugar confectionery, a culinary product, or a petfood.

The invention further relates to a method of modifying the flavour of a food composition which comprises adding a Pyridinium-Betain compound according to the invention to the food in a taste effective amount sufficient to enhance sweetness, saltiness or umami taste characteristics of the food or to reduce bitter taste characteristics of the food.

Finally, the invention also relates to a process for the preparation of these Pyridinium-Betain compounds by synthesis using 5-(hydroxymethyl)-2-furanaldehyde (HMF) and the corresponding amino acids or peptides to prepare the Pyridinium-Betain compound, or by reacting a HMF producing precursors and degradation products thereof with a corresponding amino acids or peptides under conditions sufficient to prepare the Pyridinium-Betain compound.

DETAILED DESCRIPTION OF THE PREFERRED EMBODIMENTS

Figure 1:
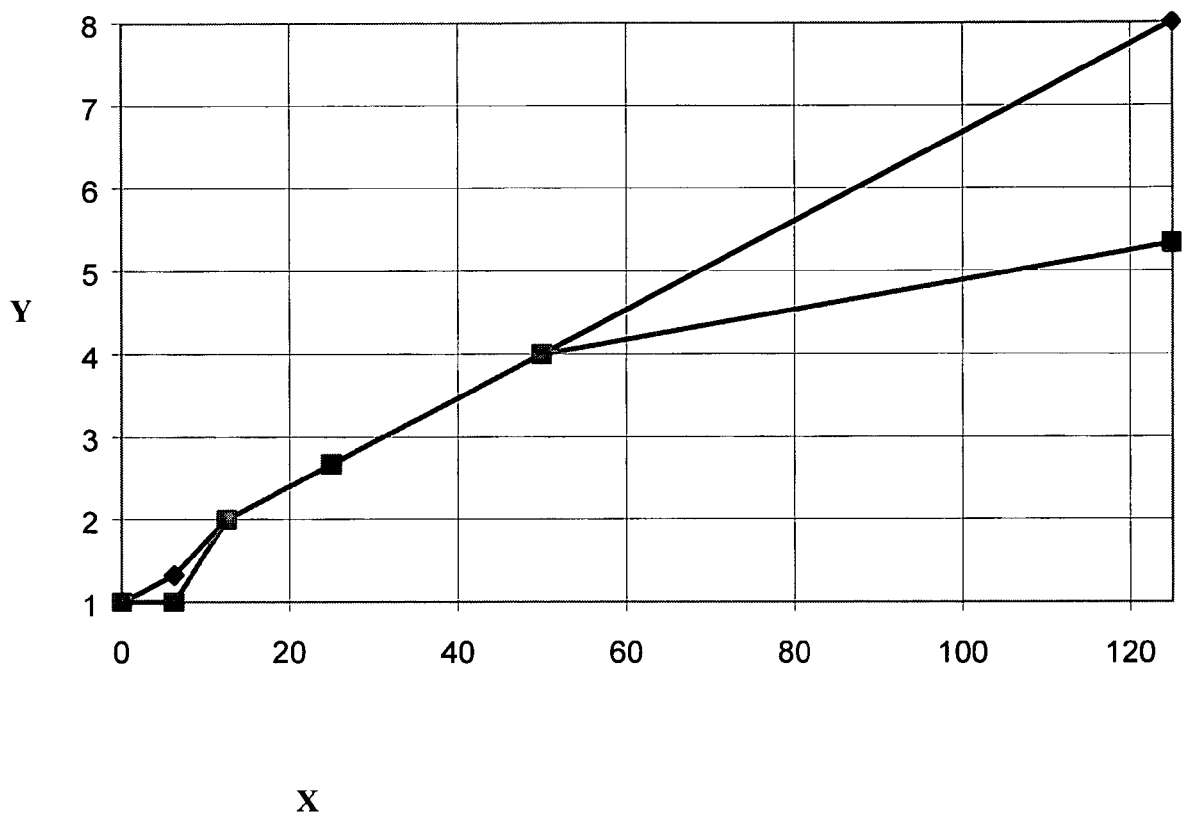
FIG. 1 is a graphical representation of the relative sweetness of the mixtures containing glucose and Alapyridaine increases with increasing amounts of a Pyridinium-Betain compound according to the invention.

As used herein, the term 'taste modifying' is defined as the ability to enhance or to reduce the sensory properties of taste compounds while 'taste modulator' is used to indicate a compound that has taste modifying properties.

As noted above, a new class of compounds, called Pyridinium-Betain compounds, has now been found and are disclosed herein by way of general formula (A). These compounds can be provided in a pure enantiomeric form or as a racemic mixture. As noted herein, the (S)-isomers of the compounds are preferred.

In this general formula, R1 can be any primary α-amino acid, for example glycine, alanine, valine, leucine, isoleucine, phenylalanine, tryptophan, methionine, serine, threonine, cysteine, tyrosine, asparagine, glutamine, aspartic acid, glutamic acid, lysine, 5-hydroxylysine, ornithine, histidine and arginine. The amino acid is connected to the structure by a bond, as shown. In this case, n is generally 0. Preferably, R1 is alanine or glycine. Other primary amino acids, in particular also β- or γ-amino acids, such as for example β-alanine or γ-amino butyric acid, can also be used. In that case, n=1 to 4 and R1 is hydrogen. The following description provides further details on several compounds according to the invention.

In a preferred embodiment of the compound of the invention, R1 is L-alanine (methyl group), Y is OH including the ionised form O⁻, Z is hydrogen and n is 0. In another preferred embodiment, R1 is glycine (hydrogen), Y is OH including the ionised form O⁻, Z is hydrogen and n is 0.

The compounds of the general formula (A) have a zwitterionic character in a broad pH range. As shown below, the zwitterionic structure (A2) dominates under slightly acidic and neutral conditions with the negative charge primarily located at the carbocylic group (X in (A)). Under basic conditions represented by the structure (A3), the negative charge may be located at the carboxylic group of the amino acid moiety (group X in (A)) and at the hydroxyl group directly attached to the pyridinium ring (group Y in (A)). Under strongly acidic conditions, both the carboxylic and hydroxyl groups are protonated, as shown in the structure (A1), i.e. the groups X and Y correspond to OH. Depending on the pH of an aqueous solution containing the compounds of the general formula (A), the structures (A1), (A2) and (A3) may exist in equilibrium.

crystals with high purity. LC/MS and 1D- and 2D-NMR spectroscopy led to the unequivocal identification of the compound as N-(1-carboxyethyl)-6-hydroxymethyl-pyridinium-3-olate (Alapyridaine).

Other useful new compounds include those of general formula (A), wherein X of COX corresponds to a further amino acid or oligopeptide attached via peptide-type (peptic) bonds. In these compounds, R1 may be a proton (R1=H). The amino acids concerned here are the same as those primary amino acids mentioned above and includes, in addition, secondary amino acids such as for example proline and 4-hydroxyproline. The useful oligopeptides may be comprised of primary and secondary amino acids. Again, the charge distribution in the molecule of the general formula (A) depend on the pH and may also include the rest of the amino acid or peptide. For example, the negative charge can be located at both the carboxylic group of the peptide and the hydroxyl group directly attached to the pyridinium ring.

The invention concerns further the use of these new Pyridinium-Betain compounds (A) as an additive to a food composition to enhance the sweetness, salty taste or umami taste of a compound that is present therein and that has such functionality. For example, it is possible to use a compound (A) to enhance the sweetness of a food composition containing for example glucose. However, it is also possible to use the same compound (A) to enhance the umami taste of a food composition containing for example monosodium glutamate (MSG). It is believed that these compounds (A) are useful because they are prepared from chiral amino acids develop taste enhancing effects α-amino acids).

The invention concerns further the addition of the new Pyridinium-Betaine compounds (A) to a food composition to reduce the bitterness of a compound therein that has such functionality. While this can be added to any food or beverage, preferred foods for addition of this compound

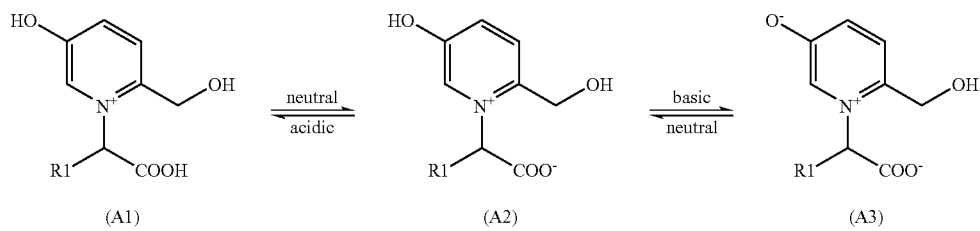

(A1)   (A2)   (A3)

R1 and Z may also be included in the charge distribution. For example, the γ-carboxylic group of glutamic acid may be negatively charged depending on the pH. Similarly, the ε-amino group of lysine as well as the guanidine group of arginine may be positively charged depending on the pH.

The above mentioned compounds are preferably obtained as reaction products from a reducing sugar with a primary amino acid or a peptide. Considering a more specific reaction and by application of a modified taste dilution analysis on HPLC fractions obtained from a thermally treated solution of glucose and L-alanine, a compound can be detected which shows taste enhancing properties upon sensory evaluation. This compound was found to be formed in higher concentrations when the hexose degradation product 5-hydroxymethyl-2-furanaldehyde (HMF) was reacted with L-alanine. After isolation by column chromatography on RP-18 material the taste compound can be obtained as include chocolate, ice-cream, a beverage, a sugar confectionery, a culinary product, or a petfood. For example, it is possible to use a compound (A) to reduce the bitterness of a food composition containing for example caffeine. The compounds (A) are prepared from non-chiral amino acids in order to develop bitter reducing effects.

For either situation, the amount desired for administration may be between 0.01 and 3000 mg/kg of the entire food composition.

The present invention also concerns a process for the preparation of these compounds by synthesis using 5-(hydroxymethyl)-2-furanaldehyde (HMF) and the corresponding amino acid or peptides. An alternative way of proceeding is to use HMF producing precursors, such mono- and polysaccharides, and the corresponding amino acid or peptides.

EXAMPLES

The following examples illustrate the invention in more detail.

Syntheses

Example 1

Synthesis of N-(1-carboxyethyl)-3-hydroxy-6-hydroxy-methyl-pyridinium inner salt [Alapyridaine]

Preparation method I: From glucose and L-alanine in water. A solution of D-glucose (200 mmol) and L-alanine (400 mmol) in phosphate buffer (400 mL; 1.0 mol/L, pH 5.0) was heated under reflux for 30 min. After cooling to room temperature, the aqueous solution was extracted with ethyl acetate (3×100 mL), the aqueous layer was freeze-dried, the residue obtained was taken up in water (20 mL) and then separated by column chromatography (4×20 cm) using RP-18 material (LiChroprep 25–40 µm) as the stationary phase and a mixture (97/3, v/v) of ammonium formate (10 mmol/l, pH 8.2) and methanol as the mobile phase. Monitoring the effluent at 252 nm, the target compound was eluted between 140 and 190 mL. After freeze-drying and rechromatpgraphy, Alapyridaine (1.2 mmol, 0.6% yield) was obtained with a purity of more than 95%.

Example 2

Synthesis of N-(1-carboxyethyl)-3-hydroxy-6-hydroxy-methyl-pyridinium inner salt [Alapyridaine]

Preparation method II: From 5-(hydroxymethyl)-2-furanaldehyde (HMF) and L-alanine. A solution of HMF (47.5 mmol) and L-alanine (40 mmol) in water/ethanol (1/1, v/v, 60 ml) was adjusted to pH 9.4 with a conc. sodium hydroxide solution (measurement run over 45 min) and then refluxed. After 24 h and 48 h, HMF (8 mmol) was added and refluxing was continued. After 72 h the reaction mixture was cooled to room temperature and freed from solvent in vacuo (45 mbar). The residue was taken up in water (30 mL), and the aqueous phase was extracted with ethyl acetate (3×50 mL). Aliquots of the aqueous phase were applied onto the top of a water-cooled glass column (4×30 cm) filled with a slurry of RP-18 material (LiChroprep 25–40 µm) in formic acid (0.1% in water). Using the same solvent mixture as the mobile phase and monitoring the effluent at 300 nm, the target compound was eluted between 280 and 460 mL as confirmed by RP-HPLC. After freeze-drying, Alapyridaine was recrystallized from ethanol (+4° C.). Final purification was performed by liquid chromatography on the same column using ammonium formate (10 mmol/l, pH 8.2) as the mobile phase. After freeze-drying twice, N-(1-carboxyethyl)-3-hydroxy-6-hydroxymethyl-pyridinium inner salt (A7) (14 mmol, 35% in yield) was obtained with a purity of more than 95%.

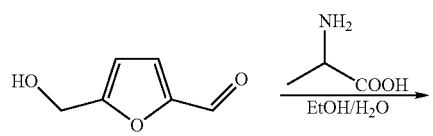

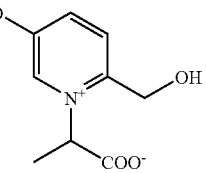

(A7)

Spectroscopic Data of Alapyridaine:

UV/VIS (ammonium formate, 10 mmol/l, pH 8.2): $\lambda_{max}$ 248 nm, 326 nm

UV/VIS (formic acid, 0.1% in water): $\lambda_{max}$ 300 nm

LC/MS (ESI+): 198 (100, [M+1]+), 220 (57, [M+Na]+), 395 (19, [2 M+1]+), 417 (29, [2 M+Na]+)

$^1$H NMR (400 MHz; DMSO-$d_6$): δ 1.59–1.61 (d, 3H, J=6.9, CH$_3$), 4.55 (s, 2H, CH$_2$), 5.01–5.06 (q, 1H, J=6.9 Hz, CH), 7.13–7.16 (dd, 1H, J=2.8, 8.9 Hz, CH), 7.38–7.41 (d, 1H, J=8.9 Hz, CH), 7.67–7.68 (d, 1H, J=2.8 Hz, CH)

$^{13}$C NMR (100 MHz; DMSO-$d_6$; HMBC, HMQC): δ 19.8 [CH$_3$], 59.1 [CH$_2$], 65.3 [CH], 128.0 [CH], 131.9 [CH], 133.2 [CH], 135.9 [C], 165.2 [CO], 170.0 [COOH]

Example 3

Synthesis of N-(1-carboxyethyl)-3-hydroxy-6-hydroxy-methyl-pyridinium inner salt [Alapyridaine]

Preparation method III: From β-fructose and L-alanine. First step, Synthesis of 5-hydroxymethylfurfural (HMF). In a flask equipped with a reflux condenser 10.0 g (55 mmol) of D-fructose, 10.0 g of Amberlist 15 resin and 2.0 g of triethylamine hydrochloride are stirred in 150 mL of n-butyl acetate and 5 mL of water. The reaction is heated at 100° C. under a nitrogen flux over a period of 2.5 h. The reaction mixture is cooled to room temperature, decanted and the organic layer is concentrated under reduced pressure to yield after filtration over neutral alumina (petroleum ether/EtOAc, 3/2) 3.3 g (26 mmol, 52% in yield, >80% purity) of 5-hydroxymethylfurfural (HMF), which is used without further purifications.

Analytical Data of HMF:

GC/MS(EI): Identical MS spectrum as compared to the reference material of HMF. Also the GC retention time of the HMF prepared was identical to that of the reference sample (RT: 26.09 min).

Preparation method III. Second step, Synthesis of Alapyridaine from HMF and L-Alanine. In a flask equipped with a reflux condenser 1.0 eq. of L-alanine and 1.2 eq. of 5-HMF are stirred in an ethanol/water mixture (50/50). The pH is adjusted to 9.4 with 32% aqueous sodium hydroxide (NaOH) solution. After 90 min stirring at room temperature, the reaction is heated to reflux for 24 h, cooled to room temperature and 0.4 eq. of HMF is added. The pH is adjusted to 9.4 with 32% aqueous NaOH hydroxide solution and after 90 min stirring at room temperature, the reaction is heated to reflux for 24 h, cooled to room temperature and 0.3 eq. of HMF is added. The pH is adjusted to 9.4 with 32% aqueous NaOH solution and after 90 min stirring at room temperature the reaction is heated to reflux for 24 h, cooled to room temperature and concentrated under reduced pressure. A chromatography on Silica gel 60 (n-BuOH/H$_2$O/AcOH, 4/4/2) and a chromatography on reversed phase RP-18 (0.5% aqueous formic acid) lead to Alapyridaine.

Example 4

Synthesis of N-carboxymethyl-3-hydroxy-6-hydroxymethyl-pyridinium inner salt [Glypyridaine]

Preparation method II: From 5-(hydroxymethyl)-2-furanaldehyde (HMF) and glycine. A solution of HMF (8.5 mmol) and glycine (12 mmol) in water/ethanol (1/1, v/v, 20 ml) was adjusted to pH 9.4 with conc. sodium hydroxide solution and then refluxed for 60 h. After cooling to room temperature the reaction mixture was freed from solvent in vacuo (45 mbar), taken up in water (10 mL), and the aqueous phase was extracted with ethyl acetate (2×10 mL). Aliquots (5 mL) of the aqueous phase were applied onto the top of a water-cooled glass column (4×30 cm) filled with a slurry of RP-18 material (LiChroprep 25–40 µm, Merck) in formic acid (0.1% in water). Using the same solvent as the mobile phase and monitoring the effluent at 300 nm, the target compound was eluted between 150 and 310 mL as confirmed by RP-HPLC/DAD. Rechromatography was performed using ammonium formate (10 mmol/l, pH 8.2) as the mobile phase on the freeze-dried residue. After freeze-drying twice, 3 N-carboxymethyl-3-hydroxy-6-hydroxymethylpyridinium inner salt (4.3 mmol, 22% in yield) was obtained with a purity of more than 95%.

Spectroscopic Data of Glypyridaine:

UV/VIS (formic acid, 0.1% in water): $\lambda_{max}$ 300 nm

LC/MS (ESI$^+$): 184 (72, [M+1]$^+$), 206 (57, [M+Na]$^+$), 228 (76, [M+2Na]$^+$), 411 (79, [2 M+2Na]$^+$), 433 (100, [2 M+3Na]$^+$)

$^1$H NMR (400 MHz; D$_2$O; TMS-P): δ 4.63 (s, 2H, CH$_2$), 4.94 (s, 2H, CH$_2$), 7.43–7.46 (dd, 1H, J=2.7, 8.9 Hz, CH), 7.56–7.58 (d, 1H, J=8.9 Hz, CH), 7.67–7.68 (d, 1H, J=2.7 Hz, CH)

$^{13}$C NMR (100 MHz; D$_2$O; TMS-P; HMBC, HMQC): δ 59.8 [CH$_2$], 60.3 [CH$_2$], 129.7 [CH], 131.0 [CH], 132.1 [CH], 138.7 [C], 165.2 [CO], 171.4 [COOH]

Example 5

Synthesis of N-(1,3-dicarboxypropyl)-3-hydroxy-6-hydroxymethyl-pyridinium inner salt (Glupyridaine)

Preparation method II. From 5-(hydroxymethyl)-2-furanaldehyde (HMF) and monosodium L-glutamate (MSG). A solution of HMF (20 mmol) and MSG (17 mmol) in water/ethanol (1/1, v/v, 40 ml) was adjusted to pH 9.4 with conc. sodium hydroxide solution and refluxed. After 36 h HMF (4 mmol) was added and refluxing was continued. After 72 h the reaction mixture was cooled to room temperature and freed from solvent in vacuo (45 mbar). The residue was taken up in water (30 mL), and the aqueous phase was extracted with ethyl acetate (3×50 mL). Aliquots of the aqueous phase were applied onto the top of a water-cooled glass column (4×30 cm) filled with a slurry of RP-18 material (LiChroprep 25–40 µm, Merck) in ammonium formate (10 mmol/l, pH 8.2). Using the same solvent mixture as the mobile phase and monitoring the effluent at 330 nm, the target compound was eluted between 220 and 320 mL as confirmed by RP-HPLC. The freeze-dried fractions were purified by automated HPLC-collection on a Jasco-HPLC-System using an analytical phenyl-hexyl column (Luna 5µ, Phenomenex) with formic acid (0.1% in water, pH 2.5) as the mobile phase. After freeze-drying twice, Glupyridaine (2.0 mmol, 12% in yield) was obtained with a purity of more than 95%.

Spectroscopic Data of Glupyridaine:

UV/VIS (ammonium formate buffer, 10 mmol/L, pH 8.2): $\lambda_{max}$ 251 nm and 330 nm LC/MS (ESI$^+$): 256 (65; [M+1]$^+$), 511 [42; 2M+1]$^+$), 533 [11; 2M+Na]$^+$), 766 [100; 3M+1]$^+$), 788 [46; 3M+Na]$^+$)

$^1$H NMR (360 MHz; D$_2$O; TMS-P): δ 2.15–2.19 (t, 2H, CH$_2$), 2.34–2.44 (m, H, CH$_a$H), 2.61–2.71 (m, H, CH$_b$H), 4.80 (s, 2H, CH$_2$), 5.28–5.32 (dd, 1H, J=5.2, 10.2 Hz, CH), 7.68–7.72 (dd, 1H, J=2.5, 8.9 Hz, CH), 7.74–7.77 (d, 1H, J=8.9 Hz, CH), 8.06–8.07 (d, 1H, J=8.9 Hz, CH)

$^{13}$C NMR (90 MHz; D$_2$O; TMS-P; HMBC, HMQC): δ 29.7 [CH$_2$], 33.6 [CH$_2$], 59.8 [CH$_2$], 69.3 [CH], 129.0 [CH], 133.5 [CH], 134.3 [CH], 143.4 [C], 160.9 [CO], 173.4 [COOH], 179.5 [COOH]

Example 6

Synthesis of (S)-N-(1-carboxyethyl)-3-hydroxy-6-hydroxy-methyl-pyridinium inner salt [(S)-Alapyridaine]

Preparation method IV: First step, Synthesis of (S)-N-(1-carboxyethyl)-2-hydroxymethyl-5-(methylamino)furan[(S)-Alafurfurylamine]. A solution of HMF (30 mmol) and L-alanine (60 mmol) in water (30 ml) was adjusted to pH 8.5 with conc. sodium hydroxide solution and stirred in a hydrogenation vessel for 30 min at room temperature. After the addition of Raney nickel (0.75 g) the solution was stirred in a hydrogen atmosphere (5 bar) for 48 h. Then, HMF (10 mmol) was added to the reaction mixture and hydrogenation was continued for another 48 h. The catalyst was filtered off, washed with methanol, and the filtrate was concentrated in vacuo. The residue was taken up in ammonium formate buffer (10 mmol/l, pH 8.2) and applied onto the top of a water-cooled glass column (4×30 cm) filled with a slurry of RP-18 material (LiChroprep 25–40 µm, Merck) in a mixture (99/1, v/v) of ammonium formate (10 m mol/l, pH 8.2) and methanol. Using the same solvent mixture as the mobile phase and monitoring the effluent at 220 nm, the target compound was eluted between 210 and 330 mL as confirmed by RP-HPLC/DAD. After freeze-drying, (S)-N-(1-carboxyethyl)-2-hydroxymethyl-5-(methyl-amino)furan (15.0 mmol, 38% in yield) was obtained.

Spectroscopic Data of (S)-Alafurfurylamine:

UV/VIS (ammonium formate, 10 mmol/l, pH 8.2): $\lambda_{max}$ 210 nm

LC/MS (ESI$^+$): 200 (49, [M+1]$^+$), 222 (42, [M+Na]$^+$), 399 (95, [2 M+1]$^+$), 421 (100, [2 M+Na]$^+$)

$^1$H NMR (250 MHz; TMS-P; D$_2$O): δ 1.42–1.45 (d, 3H, J=7.3 Hz, CH$_3$), 3.52–3.61 (q, 1H, J=7.3 Hz, CH), 4.18–4.19 (d, 2H, J=2.4 Hz, CH$_2$), 4.56 (s, 2H, CH$_2$), 6.38–6.40 (d, 1H, J=3.4 Hz, CH), 6.50–6.52 (d, 1H, J=3.4 Hz, CH)

$^{13}$C NMR (62.5 MHz; D$_2$O; TMS-P;HMQC, HMBC): δ 18.5 [CH$_3$], 44.7 [CH$_2$], 58.5 [CH$_2$], 59.7 [CH], 112.1 [CH], 115.4 [CH], 148.9 [C], 157.7 [C], 173.7 [COOH]

Preparation method IV: Second step, Oxidation of (S)-Alafurfurylamine. To a cooled (0° C.) solution of (S)-N-(1-carboxyethyl)-2-hydroxymethyl-5-(methylamino)furan (7.5 mmol) in 35 mL of water was added drop-wise a solution of bromine in methanol (6.0 mmol in 10 mL) over a period of 30 min and stirring was continued for 1 h. The resulting mixture was neutralised by the addition of a strongly basic ion exchange resin (Amberlite IRA-400 (OH⁻), Aldrich), filtered and evaporated. The residue was taken up in formic acid (0.1% in water) and applied onto the top of a water-cooled glass column (3×30 cm) filled with a slurry of RP-18 material (LiChroprep 25–40 μm, Merck) in formic acid (0.1% in water). Using the same solvent as the mobile phase and monitoring the effluent at 300 nm, the target compound was eluted between 150 and 290 mL as confirmed by RP-HPLC/DAD. Rechromatography was performed using ammonium formate (10 mmol/l, pH 8.2) as the mobile phase. After freeze-drying twice, (S)-N-(1-carboxyethyl)-3-hydroxy-6-hydroxymethyl-pyridinium inner salt (0.76 mmol, 13% in yield) was obtained.

Spectroscopic Data of (S)-Alapyridaine:

UV/VIS (ammonium formate, 10 mmol/l, pH 8.2): $\lambda_{max}$ 248 nm, 326 nm

LC/MS (ESI⁺): 198 (100, [M+1]⁺), 220 (57, [M+Na]⁺)

$^1$H NMR (360 MHz; D$_2$O; TMS-P): δ 1.85–1.87 (d, 3H, J=6.8, CH$_3$), 4.84 (s, 2H, CH$_2$), 5.39–5.44 (q, 1H, J=6.8 Hz, CH), 7.68–7.72 (dd, 1H, J=2.3, 8.6 Hz, CH), 7.76–7.78 (d, 1H, J=8.6 Hz, CH), 8.08–8.09 (d, 1H, J=2.3 Hz, CH)

Example 7

Synthesis of (R)-N-(1-carboxyethyl)-3-hydroxy-6-hydroxymethyl-pyridinium inner salt [(R)-Alapyridaine]

Preparation method IV. The same two-step procedure was applied as described for (S)-Alapyridaine, but using D-alanine as starting material.

Spectroscopic Data of (R)-Alafurfurylamine:

UV/VIS (ammonium formate, 10 mmol/l, pH 8.2): $\lambda_{max}$ 210 nm

LC/MS (ESI⁺): 200 (49, [M+1]⁺), 222 (42, [M+Na]⁺), 399 (95, [2 M+1]⁺), 421 (100, [2 M+Na]⁺)

$^1$H NMR (250 MHz; TMS-P; D$_2$O): δ 1.42–1.45 (d, 3H, J=7.3 Hz, CH$_3$), 3.52–3.61 (q, 1H, J=7.3 Hz, CH), 4.18–4.19 (d, 2H, J=2.4 Hz, CH$_2$), 4.56 (s, 2H, CH$_2$), 6.38–6.40 (d, 1H, J=3.4 Hz, CH), 6.50–6.52 (d, 1H, J=3.4 Hz, CH)

$^{13}$C NMR (62.5 MHz; D$_2$O; TMS-P; HMQC, HMBC): δ 18.5 [CH$_3$], 44.7 [CH$_2$], 58.5 [CH$_2$], 59.7 [CH], 112.1 [CH], 115.4 [CH], 148.9 [C], 157.7 [C], 173.7 [COOH]

Spectroscopic Data of (R)-Alapyridaine:

UV/VIS (ammonium formate, 10 mmol/l, pH 8.2): $\lambda_{max}$ 248 nm, 326 nm

LC/MS (ESI⁺): 198 (100, [M+1]⁺), 220 (45, [M+Na]⁺)

$^1$H NMR (360 MHz; D$_2$O; TMS-P): δ 1.85–1.87 (d, 3H, J=7.0, CH$_3$), 4.83 (s, 2H, CH$_2$) 5.39–5.44 (q, 1H, J=7.0 Hz, CH), 7.68–7.71 (dd, 1H, J=2.5, 8.6 Hz, CH), 7.75–7.78 (d, 1H, J=8.6 Hz, CH), 8.07–8.08 (d, 1H, J=2.5 Hz, CH)

Example 8

Synthesis of (S)-N-[N(1-carboxy-2-phenyl-ethyl)-carboxamido-methyl]-3-hydroxy-6-hydroxymethyl-pyridinium inner salt [(S)-GlyPhepyridaine]

Preparation method IV. The same two-step procedure was applied as described for (S)-Alapyridaine, but using the dipeptide H-Gly-Phe-OH as starting material, obtaining (S)-N-(Gly-Phe)-2-hydroxymethyl-5-(methylamino)furan (2.6 mmol, 53% yield) in the first step and the target compound (S)-GlyPhepyridaine (0.9 mmol, 36% in yield).

Spectroscopic Data of (S)-N-(Gly-Phe)-2-hydroxymethyl-5-(methylamino)furan:

LC/MS (ESI⁺): 333 (37, [M+1]⁺), 355 (68, [M+Na]⁺), 655 (82, [2 M+1]⁺), 709 (92, [2 M+2 Na]⁺), 731 (100, [2 M+3 Na]⁺)

$^1$H NMR (400 MHz; DMSO-d$_6$): δ 2.91–2.96 (dd, 1H, J=6.7, 13.5 Hz, CH$_a$H), 3.02–3.04 (d, 2H, J=4.1 Hz, CH$_2$), 3.07–3.12 (dd, 1H, J=12.8, 13.5 Hz, CH$_b$H), 3.49 (s, 2H, CH$_2$), 4.24–4.29 (dd, 1H, J=6.7, 12.8 Hz, CH), 4.34 (s, 2H, CH$_2$), 6.08–6.09 (d, 1H, J=3.1 Hz, CH), 6.16–6.17 (d, 1H, J=3.1 Hz, CH), 7.13–7.23 (m, 5H, 5×ArH)

$^{13}$C NMR (100 MHz; DMSO-d$_6$; HMQC, HMBC): δ 37.9 [CH$_2$], 45.8 [CH$_2$], 51.6 [CH$_2$], 55.0 [CH], 57.3 [CH$_2$], 107.8 [CH], 108.8 [CH], 127.1 [ArH], 128.5 [2×ArH], 129.8 [2×ArH], 136.7 [Ar], 153.3 [C], 154.8 [C], 170.4 [CO], 172.0 [COOH]

Spectroscopic Data of (S)-GlyPhepyridaine:

LC/MS (ESI⁺): 331 (100, [M+1]⁺), 661 (25, [2 M+1]⁺), 683 (33, [2 M+Na]⁺), 705 (35, [2 M+2Na]⁺), 727 (42, [2 M+3Na]⁺)

$^1$H NMR (400 MHz; DMSO-d$_6$): δ 2.81–2.86 (dd, 1H, J=8.4, 13.5, CH$_a$H), 3.09–3.13 (dd, 1H, J=3.9, 13.5 Hz, CH$_b$H), 4.17–4.22 (dd, 1H, J=3.9, 8.4 Hz, CH), 4.35 (s, 2H, CH$_2$), 5.13 (s, 2H, CH$_2$), 7.13–7.27 (m, 6H, CH, 5×ArH), 7.42–7.45 (d, 1H, J=9.3 Hz, CH), 7.68–7.69 (d, 1H, J=1.8 Hz, CH)

$^{13}$C NMR (100 MHz; DMSO-d$_6$; HMQC, HMBC): δ 37.4 [CH$_2$], 56.5 [CH$_2$], 58.0 [CH$_2$], 58.6 [CH], 126.2 [ArH], 127.5 [CH], 128.3 [2×ArH], 129.6 [2×ArH], 133.4 [CH], 136.6 [CH], 137.5 [Ar], 139.3 [C], 165.1 [CO], 166.2 [CO], 173.8 [COOH]

Sensory Analyses

Sensory panel training: Assessors were trained to evaluate the taste of aqueous solutions (1 mL each) of the following standard taste compounds by using a triangle test: saccharose (50 mmol/L) for sweet taste; lactic acid (20 mmol/L) for sour taste; NaCl (12 mmol/L) for salty taste; caffeine (1 mmol/L) for bitter taste; monosodium glutamate (MSG, 8 mmol/L, pH 5.7) for umami taste; tannin (gallustannic acid; 0.05%) for astringency. Sensory analyses were performed in a sensory panel room at 22–25° C. on three different sessions.

Taste thresholds: The taste thresholds of the tastants or mixtures containing basic tastants plus Pyridinium-Betains were determined in a triangle test using Evian® mineral water as the solvent at a defined pH (H. Wieser and H.-D. Belitz, *Z. Lebensm. Unters. Forsch.* 1975, 159, 65–72). The samples (3 mL) were presented in order of increasing concentrations (serial 1:1 dilutions). The threshold values evaluated in two different sessions were averaged. The values between individuals and separate sessions differed not more than one dilution step, i.e. a threshold value of 0.5 mmol/L for caffeine represents a range from 0.25 to 1.0 mmol/L. Prior to sensory analysis, the purity of the synthetic taste compounds was proven by LC/MS and $^1$H NMR spectroscopy.

Determination of iso-intensity: The taste intensities of aqueous (Evian®) solutions containing a basic tastant, such as glucose and MSG, for example, in constant concentrations and the compounds of the general formula (A), for example Alapyridaine, in various concentrations were compared with those of a solution containing the basic tastant only. To achieve this, triangle tests were performed with two glass vials containing the basic tastant in constant concentrations, and one glass vial containing a stepwise 1:1-diluted mixture of basic tastant and Alapyridaine. The sensory panel was asked to detect the dilution at which all three glass vials showed the same intensity in taste. The relative taste strength (taste enhancing factor) of a mixture containing the basic tastant and Alapyridaine was related to the basic tastants glucose, MSG, or other tastants, respectively, as standard substances, and was determined as the ratio of the concentrations c of iso-intensely tasting solutions of the basic tastant, such as glucose (glc), and the mixture containing tastant plus Pyridinium-Betain, i.e.

$$f_{glc,g}(c_{glc}) = c_{glc}/c_{glc+Alapyridaine}$$

Surprisingly, certain Pyridinium-Betains of the general formula (A) were found to significantly lower the taste thresholds of various types of taste molecules. This taste enhancing effect is illustrated in examples.

Example 9

Enhancement of the Sweet Taste Modality

The sweet taste thresholds of equimolar mixtures of sweet tasting compounds and various Pyridinium-Betaines were determined by a triangle test using EVIAN® mineral water as the solvent. The sensorial evaluations were performed at different pH values. The equimolar mixture of Alapyridaine and sucrose at pH 7.0 was evaluated with a 4-fold lower sweet threshold concentration than pure sucrose (Table 1). At pH 9.0 the same solution showed an 8-fold lower threshold. In contrary to the these results, the pH 5.0 solution shows a sour taste that probably covers the sweet taste. Comparable results were obtained with Phepyridaine, which has about the same threshold reduction, but imparts a rubber-like off-taste in concentrations above 3 mmol/kg. Glupyridaine showed, compared to Alapyridaine, in mixture with sucrose a far higher sweet threshold, both at pH 7.0 and pH 9.0. These results indicate that the Pyridinium-Betaines are most active in basic environments, a smaller activity was found at neutral pH, whereas in sour environment, the taste-enhancement is associated with a sour taste. This is most likely due to the various forms of the Pyridinium-Betaines, i.e., for pH values>5.5 they exist as deprotonized olates with counter ions such as e.g. ammonium, whereas the hydroxy-function is protonized at pH<5.5.

TABLE 1

Comparison of sweet taste detection thresholds of various sucrose/Pyridinium Betaine mixtures

| Taste enhancer | pH value | Taste quality | Sweet detection threshold [mmol/kg water] | Threshold decrease[a] |
|---|---|---|---|---|
| Alapyridaine | 5.0 | sweet/sour | 3.0 | 4.0 |
| | 7.0 | sweet | 3.0 | 4.0 |
| | 9.0 | sweet | 1.5 | 8.0 |
| Phepyridaine[b] | 7.0 | sweet | 3.0 | 4.0 |
| | 9.0 | sweet | 1.5 | 8.0 |
| Glupyridaine | 7.0 | sweet | 12.0 | — |
| | 9.0 | sweet | 6.0 | 2 |

[a]The threshold of sucrose in water is 12.5 mmol/L.
[b]The sweetness is associated with a rubber-like taste in concentrations higher than 3 mmol/L.

Alapyridaine is able to reduce the sweet threshold of glucose 16-fold at pH 7.0 and pH 9.0, whereas at pH 5.0 a gain the sweet taste perception is associated by as our taste (Table 2). Phepyridaine shows the same threshold reduction, but imparts a rubber-like taste in concentrations higher than 3 mmol/L. Using the dipeptide derivative (S)-GlyPhepyridaine as a taste-enhancer leads to a 16-fold threshold reduction compared to glucose.

TABLE 2

Comparison of sweet taste detection thresholds of various glucose/Pyridinium-Betaine mixtures

| Taste enhancer | pH value | Taste quality | Sweet detection threshold [mmol/kg water] | Threshold decrease[a] |
|---|---|---|---|---|
| Alapyridaine | 5.0 | sweet/sour | 6.0 | 8.0 |
| | 7.0 | sweet | 3.0 | 16.0 |
| | 9.0 | sweet | 3.0 | 16.0 |
| Phepyridaine[b] | 7.0 | sweet | 3.0 | 16.0 |
| (S)-GlyPhepyridaine | 7.0 | sweet | 3.0 | 16.0 |

[a]The threshold of glucose in water is 50.0 mmol/L.
[b]The sweetness is associated with a rubber-like taste in concentrations higher than 3 mmol/L.

Besides the two carbohydrates, the sweet amino acid L-alanine was also tested with Alapyridaine. Again, the best impact on sweet taste perception was found for the mixture at pH 9.0, resulting in an 8-fold lower threshold. At pH 7.0 a 4-fold reduction of the sweet threshold was found, whereas at pH 5.0 only a slight reduction was determined (Table 3).

TABLE 3

Comparison of sweet taste detection thresholds of various L-alanine/Pyridinium-Betaine mixtures

| Taste enhancer | pH value | Taste quality | Sweet detection threshold [mmol/kg water] | Threshold decrease[a] |
|---|---|---|---|---|
| Alapyridaine | 6.0 | sweet | 6.0 | 2.0 |
| | 7.0 | sweet | 3.0 | 4.0 |
| | 9.0 | sweet | 1.5 | 8.0 |

[a]The threshold of L-alanine in water is 12.5 mmol/L.

Example 10

Enhancement of the Umami Taste Modality

Pyridinium-Betaines not only enhance the sweet taste perception, but also the umami taste. As shown in Table 4, Alapyridaine decreases the umami threshold in the equimolar mixture with monosodium glutamate (MSG) 4-fold. Comparable results were determined for Phepyridaine, Glupyridaine and (S)-GlyPhepyridaine. It was also shown, that in contrary to the sweet experiments, the pH value does not seem to significantly influence the activity of the Pyridinium-Betaines on the umami taste.

TABLE 4

Comparison of umami taste detection thresholds of various MSG/Pyridinium-Betaine mixtures

| Taste enhancer | pH value | Taste quality | Umami detection threshold [mmol/kg water] | Threshold decrease[a] |
|---|---|---|---|---|
| Alapyridaine | 5.0 | umami | 0.4 | 4.0 |
|  | 7.0 | umami | 0.4 | 4.0 |
|  | 9.0 | umami | 0.4 | 4.0 |
| (S)-GlyPhepyridaine | 7.0 | umami | 0.2 | 8.0 |
| Phepyridaine | 7.0 | umami | 0.4 | 4.0 |
| Glupyridaine | 7.0 | umami | 0.4 | 4.0 |

[a]The threshold of MSG in water is 1.5 mmol/L.

Example 11

Enhancement of the Salty Taste Modality

Pyridaine Betaines were also investigated for taste enhancement of the salty taste modality using sodium chloride. As shown in Table 5, all tested compounds were able to reduce the salt detection threshold 5-fold.

TABLE 5

Comparison of salt taste detection thresholds of various NaCl/Pyridinium-Betaine mixtures (pH 7.0)

| Taste enhancer | Taste quality | Salt detection threshold [mmol/kg water] | Threshold decrease[a] |
|---|---|---|---|
| Alapyridaine | salty | 2.0 | 5.0 |
| Phepyridaine | salty | 2.0 | 5.0 |
| Glypyridaine | salty | 2.0 | 5.0 |
| Argpyridaine[b] | salty | 2.0 | 5.0 |

[a]The threshold of salt (NaCl) in water is 10.0 mmol/L.

Example 12

Enhancement of Sweet Taste (Iso-intensity)

The taste enhancing potential of the compounds of the general formula (A) was further evidenced by evaluating solutions of equal intensity (iso-intensity) containing glucose or mixtures of glucose and, for example, Alapyridaine in various concentrations. As shown in FIG. 1, the relative sweetness of the mixtures containing glucose and Alapyridaine increases with increasing amount of the Pyridinium-Betain compound. This shows the taste enhancing potential of Alapyridaine on the sweet taste of glucose, which is more pronounced at lower glucose concentrations (e.g. 80 mmol/L). A solution containing 80 mmol/kg glucose and 125 mmol/kg Alapyridaine is 8-fold sweeter than a solution containing 80 mmol/kg glucose. In other words, this solution has to be diluted 3-times to match the sweetness of the standard solution, i.e. in this case a solution containing 10 mmol/kg glucose and 16 mmol Alapyridaine is as sweet as the standard solution (80 mmol/kg glucose). The maximum sweetness of the higher concentrated glucose/Alapyridaine mixture (267 and 125 mmol/kg) lies 5.3-fold higher than the reference solution (267 mmol/kg).

FIG. 1 shows the relative sweetness $f_{glc}$ (Y axis) of iso-intense solutions of glucose (♦: 80 mmol/L or ■: 267 mmol/L in water) and mixtures containing glucose and Alapyridaine in various concentrations (the X axis represents the concentration of Alapyridaine in mmol/L water).

Example 13

Enhancement of Umami Taste (Iso-intensity)

Figure 2:
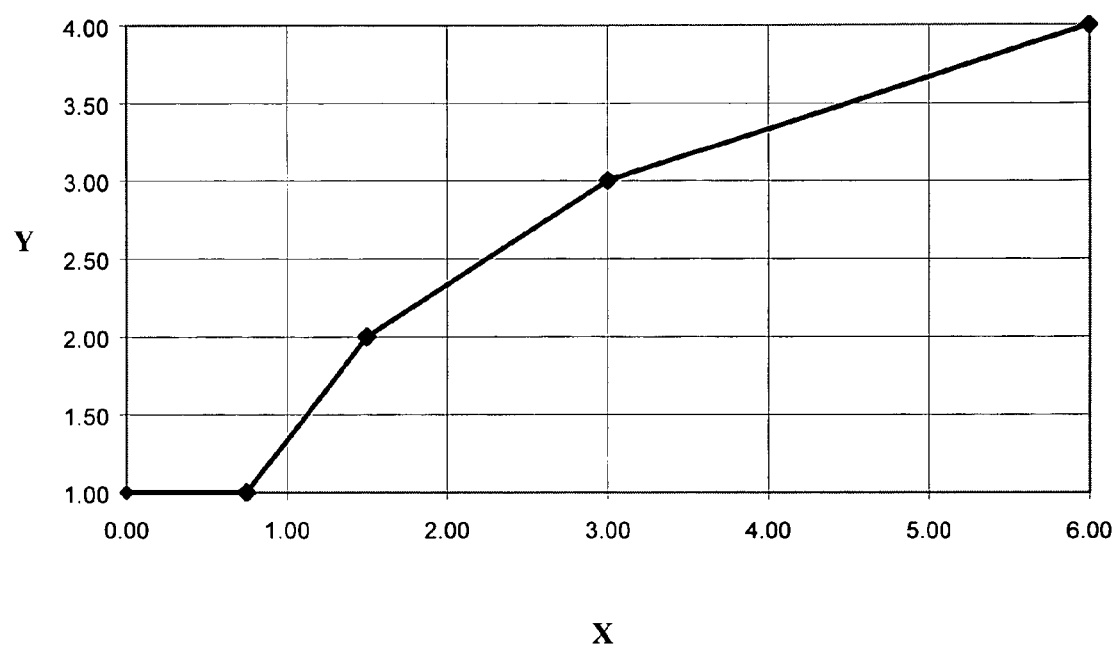
FIG. 2 is a graph that shows that the maximum umami-taste intensity was achieved with a solution containing 1.5 mmol/kg MSG and 6.0 mmol/kg Alapyridaine.

The same sensory experiment was performed with monosodium L-glutamate (MSG) and Alapyridaine. As shown in FIG. 2, the maximum umami-taste intensity (4-fold higher) was achieved with a solution containing 1.5 mmol/kg MSG and 6.0 mmol/kg Alapyridaine. That means that a solution of 0.4 mmol/kg MSG and 1.5 mmol/kg Alapyridaine has the same umami intensity as the standard umami-solution (1.5 mmol/kg water).

FIG. 2 shows the relative umami taste $f_{glu}$ (Y axis) of iso-intense solutions of MSG (1.5 mmol/L) and mixtures containing MSG and Alapyridaine in various concentrations (the X axis represents the concentration of Alapyridaine in mmol/L water).

Example 14

Enhancement of Salty Taste

The salt-intensities of various NaCl/Pyridinium-Betaine mixtures (20 mmol/L each) were compared to a 20 mmol/L NaCl standard solution. The sensory panel was asked to rank the salt-intensities of these solutions on a scale from 0 (not salty) to 5 (very salty), while the reference NaCl-solution was ranked as 1. As listed in Table 6, the most intense salty taste was found in the solution containing NaCl and Alapyridaine, as well as in the triple mixture with L-arginine. A slight impact was found for Argpyridaine and L-arginine.

TABLE 6

Comparison of the salty intensities of various NaCl/Pyridinium-Betaine mixtures (pH 7.0)

| Compound(s) (20 mmol/L each) | Taste quality | Salt-intensity |
|---|---|---|
| NaCl | salty | 1.0 |
| NaCl + L-Arginine (L-Arg) | salty | 2.0 |
| NaCl + Alapyridaine | salty | 4.0 |
| NaCl + Argpyridaine | salty | 2.5 |
| NaCl + Alapyridaine + L-Arg | salty | 5.0 |
| L-Arginine (L-Arg) | — | 0.0 |
| Alapyridaine | — | 0.0 |
| Argpyridaine | — | 0.0 |
| Alapyridaine + L-Arg | — | 0.0 |

Surprisingly, certain Pyridinium-Betains of the general formula (A) were found to significantly reduce the taste intensity of various types of bitter-tasting molecules.

This taste bitter-blocking effect is illustrated in the following examples.

Example 15

Bitter-blocking Effect on L-phenylalanine

The tasteless Pyridinium-Betaines Glypyridaine, β-Alapyridaine and Gabapyridaine, built from non-chiralic amino acids, were tested for their bitter-blocking activity on L-phenylalanine. As shown in Table 7, solutions composed of equimolar amounts of one of the said Pyridinium-Betains and L-phenylalanine lead to complete loss of the bitter taste.

TABLE 7

Comparison of detection thresholds of L-phenylalanine (L-Phe) and mixtures (1/1) of L-Phe and Pyridinium-Betaines (pH 7.0)

| Compound(s) (conc. 32 mmol/L) | Taste quality | Detection threshold (mmol/L water) |
|---|---|---|
| L-Phenylalanine (L-Phe) | bitter | 16.0 |
| L-Phe + Glypyridaine | no taste | — |
| L-Phe + β-Alapyridaine | no taste | — |
| L-Phe + Gabapyridaine | no taste | — |

Example 16

Concentration-dependent Bitterness Reduction with Glypyridaine

Instead of working with low concentrated solutions at the bitter threshold, another series of experiments use carried out using more concentrated solutions of various bitter compounds to evaluate the bitter-blocking properties of Pyridinium-Betaines based on non-chiral amino acids. A trained sensory panel was asked to rank the bitter intensity of various bitter compounds compared to solutions containing the same concentration of these compounds plus various amounts of the said Pyridinium-Betaines on a scale from 0 (no bitterness) to 5 (strong bitterness).

Figure 3:
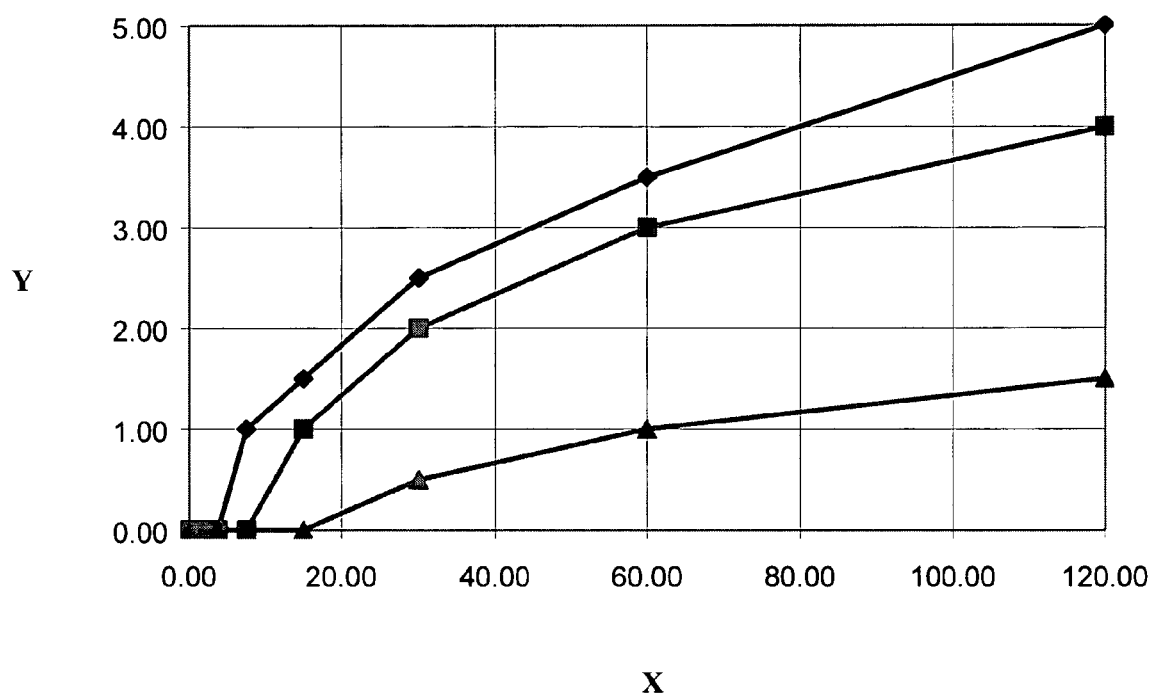
FIG. 3 illustrates that a compound according to the invention, glypyridaine, is able to strongly reduce the bitterness of solutions containing the bitter-tasting dipeptide H-Gly-Leu-OH.

As shown in FIG. 3, Glypyridaine is able to strongly reduce the bitterness of solutions containing the bitter-tasting dipeptide H-Gly-Leu-OH, even if lower concentrations of the Glypyridaine were used. The strong bitter taste of a solution containing 120 mmol/kg dipeptide and Glypyridaine in the molar ratio 2:1 was almost suppressed.

FIG. 3 shows the bitter taste intensity (Y axis: 0, no bitterness; 5, very bitter) of solutions (mmol/kg water) of H-Gly-Leu-OH (♦) and mixtures containing H-Gly-Leu-OH and Glypyridaine in the concentration ratios of 10:1 (■) and 2:1 (▲) (the X axis represents the concentration of H-Gly-Leu-OH in mmol/kg water).

Table 8 shows the bitter taste reducing potential of Glypyridaine at various concentration ratios with L-Phenylalanine, H-Gly-Leu-OH, caffeine, salicine, and naringine. The bitter-reducing effect was most pronounced with L-Phenylalanine, the dipeptide H-Gly-Leu-OH, and caffeine. For example the 10:1 mixture of L-Phenylalanine and Glypyridaine was weaker in bitterness (score 3) as compared to pure L-Phenylalanine (score 5).

TABLE 8

Bitter taste reduction effect of Glypyridaine at various concentration ratios.

| Bitter compound | Bitter tastant concentrations (mmol/L water) | Ratio bitter tastant to Glypyridaine | Bitter taste intensity[a] |
|---|---|---|---|
| L-Phenylalanine | 20/40/80 | L-Phe | 2/4/5 |
| | | 10:1 | 0.5/2/3 |
| | | 1:1 | 0/0/0.5 |
| H-Gly-Leu-OH | 30/60/120 | Dipeptide | 2.5/3.5/5 |
| | | 10:1 | 2/3/4 |
| | | 2:1 | 0.5/1/1.5 |
| Caffeine | 4/8/16 | Caffeine | 3/4.5/5 |
| | | 5:1 | 1.5/2/3 |
| | | 1:1 | 0.5/1.5/2 |
| Salicine | 0.8/1.6/3.2 | Salicine | 3/4.5/5 |
| | | 1:1 | 1/2/3 |

TABLE 8-continued

Bitter taste reduction effect of Glypyridaine at various concentration ratios.

| Bitter compound | Bitter tastant concentrations (mmol/L water) | Ratio bitter tastant to Glypyridaine | Bitter taste intensity[a] |
|---|---|---|---|
| Naringine | 0.06/0.13/0.25 | Naringine | 2.5/4/5 |
| | | 1:1 | 1/2/3 |

[a]Bitter taste intensity:
0, no bitterness;
5, strongly bitter

Example 17

Concentration-dependent Bitterness Reduction of Coffee with Glypyridaine

Figure 4:
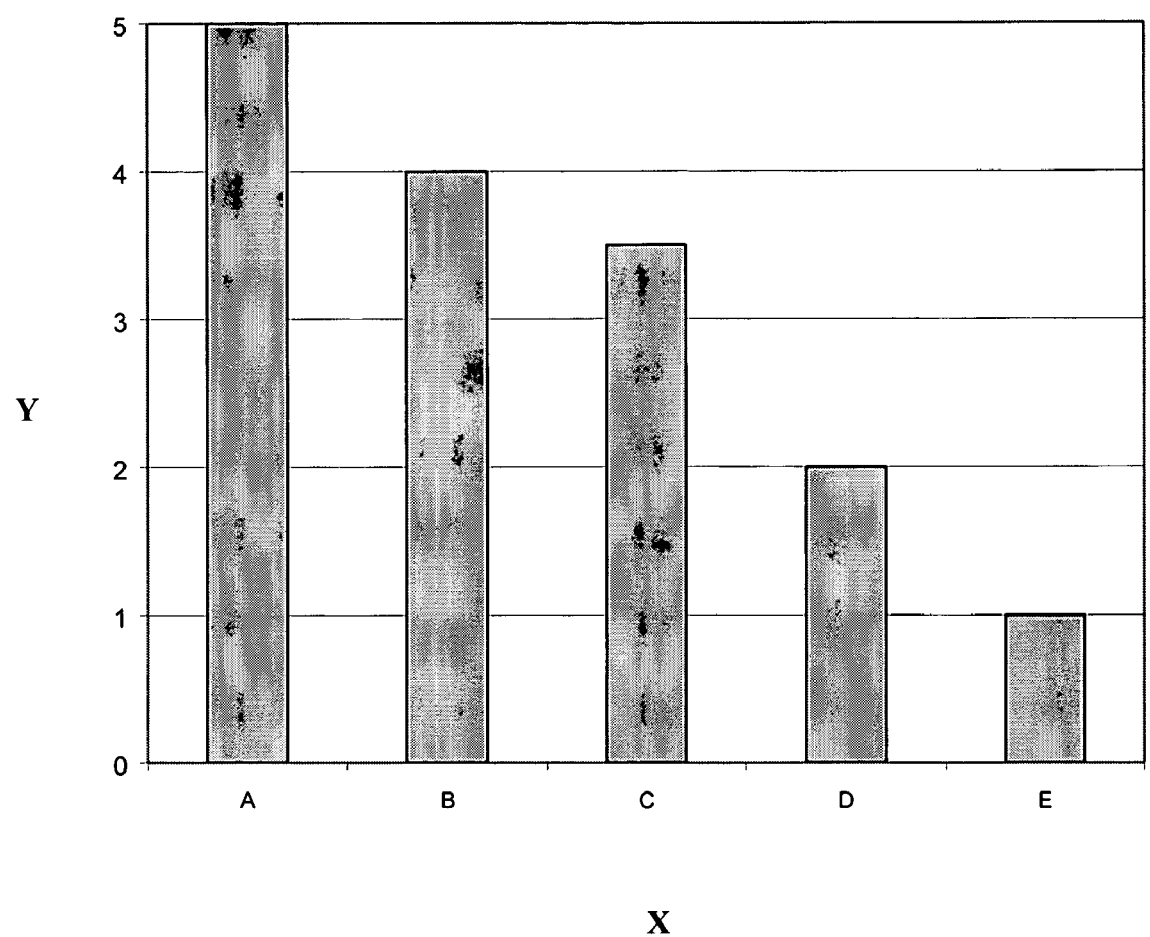
FIG. 4 illustrates the addition of different concentrations of Glypyridaine to coffee to demonstrate its bitterness reducing qualities.

The addition of different concentrations of Glypyridaine to coffee showed bitter-reducing effects (FIG. 4). For example, adding 2.0 m mol/L of Glypyridaine to coffee drastically reduced its bitter taste from 5 to 2 on a scale from 0 (no bitterness) to 5 (very bitter).

FIG. 4 shows the bitter taste intensity (Y axis: 0, no bitterness; 5, very bitter) of coffee brew (A, 40 g/L) and mixtures of coffee brew spiked with increasing amounts of Glypyridaine (mmol/L), i.e. 0.02 (B), 0.2 (C), 2.0 (D), and 6.8 (D) on the X axis.

Surprisingly, it was found that only the (S)-enantiomeric forms of the compounds of the general formula (A) function as taste enhancers. The taste enhancing effect of (S)-Alapyridaine is illustrated in examples.

Example 18

Umami Taste Enhancement with (S)-Alapyridaine

As shown in Table 9, the mixture of (+)-(S)-Alapyridaine and MSG has the lowest umami detection threshold of 0.2 mmol/kg water, while (−)-(R)-Alapyridaine does not have any taste enhancing impact. The umami threshold of the racemate has been one dilution above that found for (+)-(S)-Alapyridaine, which was to be expected as this mixture has only of half of the amount of the active (+)-(S)-Alapyridaine.

TABLE 9

Comparison of detection thresholds of mixtures containing MSG and enantiomers of Alapyridaine

| Compound(s) | Taste quality | Detection threshold [mmol/kg water] | Threshold decrease |
|---|---|---|---|
| MSG | umami | 1.5 | — |
| MSG + Alapyridaine | umami | 0.4 | 4 |
| MSG + (−)-(R)-Alapyridaine | umami | 1.5 | — |
| MSG + (+)-(S)-Alapyridaine | umami | 0.2 | 8 |

Example 19

Sweet Taste Enhancement with (S)-Alapyridaine

Table 10 shows that (+)-(S)-Alapyridaine is the active form as its mixture with sucrose was evaluated with a 8-fold lower sweet threshold as compared to a pure sucrose solution. (−)-(R)-Alapyridaine does not alter the sweet taste perception of sucrose.

TABLE 10

Comparison of detection thresholds of mixtures containing sucrose and Alapyridaine enantiomers

| Compound(s) | Taste quality | Detection threshold [mmol/kg water] | Threshold decrease |
|---|---|---|---|
| Sucrose | sweet | 12.5 | — |
| Sucrose + Alapyridaine | sweet | 3.0 | 4 |
| Sucrose + (−)-(R)-Alapyridaine | sweet | 12.5 | — |
| Sucrose + (+)-(S)-Alapyridaine | sweet | 1.5 | 8 |

Example 20

Salty Taste Enhancement with (S)-Alapyridaine

As shown in Table 11, (+)-(S)-Alapyridaine was responsible for the taste-enhancing effect, while (−)-(R)-Alapyridaine did not alter the taste of the aqueous salt solution.

TABLE 11

Comparison of detection thresholds of mixtures containing salt and enantiomers of Alapyridaine

| Compound(s) | Taste quality | Detection threshold [mmol/kg water] | Threshold decrease |
|---|---|---|---|
| Salt (NaCl) | salty | 10.0 | — |
| NaCl + Alapyridaine | salty | 2.0 | 5 |
| NaCl + (−)-(R)-Alapyridaine | salty | 10.0 | — |
| NaCl + (+)-(S)-Alapyridaine | salty | 2.0 | 5 |

Example 21

Identification and Quantification of Alapyridaine in Beef Broth

Beef meat (purchased in a local shop; 1.0 kg), cut into small pieces, was boiled in water (2 L) for 3 h. After cooling to room temperature, the mixture was filtered and the aqueous solution was extracted with ethyl acetate (5×200 mL). To remove high-molecular weight compounds, the aqueous phase was separated by ultrafiltration using regenerated cellulose ultrafiltration membranes (Ø 63.5 mm, YM10, Millipore) with a cut-off of 1000 Da. The low-molecular weight fraction was freeze-dried, and aliquots (1.0 g) of the non-volatile residue (15.6 g) was fractionated by gel permeation chromatography (GPC) using a water-cooled glass column (400×55 mm, Pharmacia) filled with a slurry of Sephadex G-15 (Pharmacia) in aqueous acetic acid (0.1 mol/L). Chromatographic separation was monitored by means of an UV/VIS detector ($\lambda=254$ nm) and the effluent (2.0 m/min) was collected into 15 mL fractions. These fractions were freeze-dried, the residues were dissolved in water, membrane-filtered, and then analysed by HPLC (4.6× 250 mm; BIO-TEK Kontron Instruments) using RP-18 material (ODS-Hypersil, 5 µm, 10 nm, Shandon) as the stationary phase. Using a gradient of aqueous trifluoroacetic acid (0.1% in water) and methanol as the mobile phase and monitoring the effluent (0.8 mL/min) by means of a diode array detector or a mass spectrometric detector operating in the ESI mode, respectively, Alapyridaine was detected in the GPC fraction eluting between 5.5 and 6.5 h by comparison of the UV/VIS and the LC/MS spectra, the retention times as well as the sensory properties with those obtained for the synthetic reference compound. Quantitative analysis, performed by comparing the peak area obtained at $\lambda=298$ nm with those of a defined standard solution of the reference compound in methanol, revealed that Alapyridaine is present in beef broth in concentrations of 419 µg/L, thus verifying the natural occurrence of this Pyridinium-Betain in beef broth and suggesting that in general Pyridinium-Betains may occur in thermally treated foods.

Example 22

Effect of Alapyridaine on the Taste Profile of a "Beef Broth" Taste Recombinate

The beef taste recombinate (K. Shima et al., *J. Agric. Food. Chem.* 1998, 46, 1465–1468) consisting of 16 amino acids, 4 sugars, three 5'-nucleotides, 3 carbonic acids, 3 salts, and 4 other compounds was used as a sample having a basic brothy taste at pH 5, i.e. (in mg/L water) threonine (68), serine (38), MSG (64), proline (16), glycine (56), alanine (192), valine (34), methionine (20), isoleucine (16), leucine (28), tyrosine (38), phenylalanine (26), lysine hydrochloride (44), histidine (38), arginine (32), taurine (248), ribose (4), mannose (8), fructose (20), glucose (40), IMP.2Na.5H$_2$0 (424), GMP.2Na7H$_2$0 (80), AMP (60), pyroglutamic acid (1296), lactic acid (3567), succinic acid (98), NaCl (854), KCl (3940), MgCl$_2$.6H$_2$0 (1104), CaCl$_2$.2H$_2$0 (14), H$_3$PO$_4$, carnosine (912), creatine (1106), and creatinine (572) were dissolved in 1 L of water, and the pH was adjusted to 5.0.

The sensory panel was asked to score the given taste qualities of the biomimetic beef taste recombinate on a scale from 0 (not detectable) to 5 (strong). To study the influence of Alapyridaine on the taste qualities of that recombinate, a triangle test was performed with two glass vials containing the pure beef taste recombinate, and one glass vial containing the beef taste recombinate plus a known amount of Alapyridaine. The sensory panel was asked to detect the Alapyridaine-containing solution out of the three vials and to rank the given taste qualities on a scale from 0 to 5 in their intensity.

Figure 5:
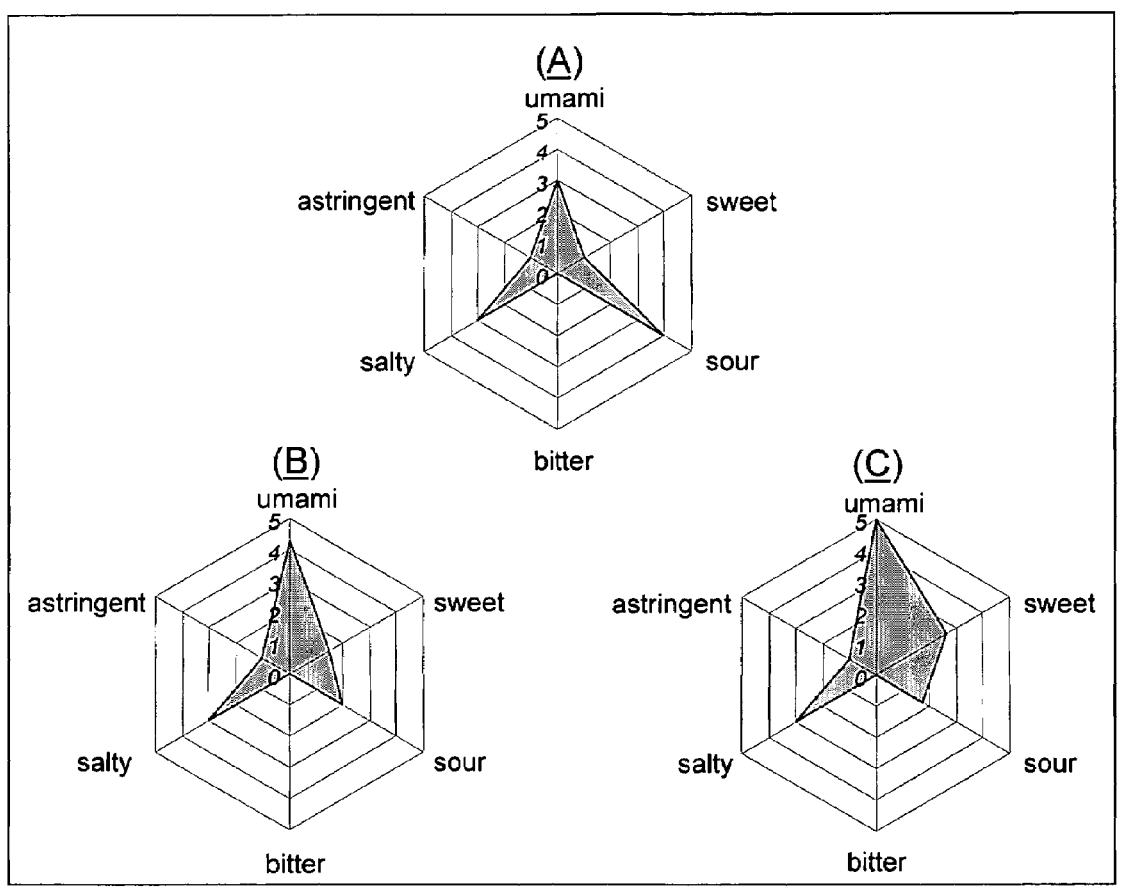
FIG. 5 shows the sensory profiling of a taste recombinate (A) when 0.5 mg/L Alapyridaine (B) or 5.0 mg/L Alapyridaine (C) are added.

The taste of the reference sample (A) was described as sour, umami, salty and weak sweet and astringent (FIG. 5). Addition of Alapyridaine (0.5 mg/L) to the recombinate (A) increased the umami character and decreased the sour note in sample (B). Further increase of Alapyridaine (5 mg/L) gave rise to more intense umami, sweet and salty taste and a reduced sourness in sample (C) (FIG. 5).

FIG. 5 shows the sensory profiling of the taste recombinate (A) and the mixtures with 0.5 mg/L Alapyridaine (B), and 5.0 mg/L Alapyridaine (C).

What is claimed is:

1. A Pyridinium-Betain compound having the general formula (A):

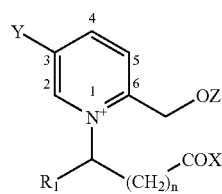

wherein R1 is H or an amino acid side chain that is attached to the structure,

X is OH or its ionised form O⁻,

Y is OH, SH, or their ionised forms O⁻ and S⁻,

Z is H, an alkyl group, or a glycosidic group, or a phosphate, and n is an integer of 0 to 4 to represent the chain length of the compound.

2. The compound of claim 1 wherein a counter-ion of sodium, potassium, ammonium, calcium, magnesium, chloride, nitrate, carbonate, sulphate, or phosphate is associated with the compound.

3. The compound of claim 1 wherein R1 is the amino acid side chain of glycine, alanine, valine, leucine, isoleucine, phenylalanine, tryptophan, methionine, serine, threonine, cysteine, tyrosine, asparagine, glutamine, aspartic acid, glutamic acid, lysine, 5-hydroxylysine, ornithine, histidine or arginine.

4. The compound of claim 1, wherein R1 is the amino acid side chain of L-alanine, Y is OH or O⁻, Z is hydrogen, and n is 0.

5. The compound of claim 1, wherein R1 is the amino acid side chain of glycine, Y is OH or O⁻, Z is hydrogen atom, and n is 0.

6. The compound of claim 1, in the form of its S-isomer.

7. A food composition comprising a food and a Pyridinium-Betain compound according to claim 1 in a taste effective amount sufficient to enhance sweetness, saltiness or umami taste characteristics of the food or to reduce bitter taste characteristics of the food.

8. The food composition of claim 7, wherein the food is chocolate, ice-cream, a beverage, a sugar confectionery, a culinary product, or a petfood.

9. The food composition of claim 7, wherein the Pyridinium-Betain compound is present in an amount of between 0.01 and 3000 mg/kg of the composition.

10. The food composition of claim 7, wherein the compound is in the form of its S-isomer.

11. A method of modifying the flavour of a food composition which comprises adding to the food composition a Pyridinium-Betain compound according to claim 1 in a taste effective amount sufficient to enhance sweetness, saltiness or umami taste characteristics of the food or to reduce bitter taste characteristics of the food.

12. The method of claim 11, wherein the food is chocolate, ice-cream, a beverage, a sugar confectionery, a culinary product, or a petfood.

13. The method of claim 11, wherein the Pyridinium-Betain compound is present in an amount of between 0.01 and 3000 mg/kg of the composition.

14. A process for the preparation of a Pyridinium-Betain compound according to claim 1, by synthesis using 5-(hydroxymethyl)-2-furanaldehyde and amino acids or peptides to prepare the Pyridinium-Betain compound.

15. A process for the preparation of a Pyridinium-Betain compound according to claim 1, by reacting a 5-(hydroxymethyl)-2-furanaldehyde producing precursors and degradation products thereof with amino acids or peptides under conditions sufficient to prepare the Pyridinium-Betain compound.

16. The process of claim 14 wherein the 5-(hydroxymethyl)-2-furanaldehyde precursor is a mono- or polysaccharide.

17. A Pyridinium-Betain compound having the general formula (A)

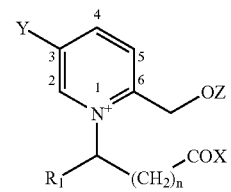

wherein R1 is H or an amino acid side chain that is attached to the structure,

X is an amino acid or oligopeptide, comprising primary and secondary L-amino acids, and is attached via peptide bonds, Y is OH, SH, or their ionised forms O⁻ and S⁻, Z is H, an alkyl group, or a glycosidic group, or a phosphate, and n is an integer of 0 to 4 to represent the chain length of the compound.

* * * * *